United States Patent
Jacobsen et al.

(10) Patent No.: US 11,337,963 B2
(45) Date of Patent: May 24, 2022

(54) COMPOSITIONS AND METHODS OF ENHANCING 5-HYDROXYTRYPTOPHAN BIOAVAILABILITY

(71) Applicant: Duke University, Durham, NC (US)

(72) Inventors: Jacob P. R. Jacobsen, Durham, NC (US); Marc G. Caron, Hillsborough, NC (US)

(73) Assignee: Duke University, Durham, NC (US)

( * ) Notice: Subject to any disclaimer, the term of this patent is extended or adjusted under 35 U.S.C. 154(b) by 35 days.

(21) Appl. No.: 15/733,423

(22) PCT Filed: Jan. 28, 2019

(86) PCT No.: PCT/US2019/015391
§ 371 (c)(1),
(2) Date: Jul. 24, 2020

(87) PCT Pub. No.: WO2019/148087
PCT Pub. Date: Aug. 1, 2019

(65) Prior Publication Data
US 2021/0346345 A1    Nov. 11, 2021

Related U.S. Application Data

(60) Provisional application No. 62/623,073, filed on Jan. 29, 2018, provisional application No. 62/743,816, filed on Oct. 10, 2018.

(51) Int. Cl.
*A61K 31/405*    (2006.01)
*A61K 31/135*    (2006.01)
*A61K 31/138*    (2006.01)
*A61K 31/15*    (2006.01)
*A61K 31/198*    (2006.01)
*A61K 31/343*    (2006.01)
*A61K 31/4406*    (2006.01)
*A61K 31/4525*    (2006.01)
*A61K 31/454*    (2006.01)
*A61K 31/495*    (2006.01)
*A61K 31/496*    (2006.01)

(52) U.S. Cl.
CPC .......... *A61K 31/405* (2013.01); *A61K 31/135* (2013.01); *A61K 31/138* (2013.01); *A61K 31/15* (2013.01); *A61K 31/198* (2013.01); *A61K 31/343* (2013.01); *A61K 31/4406* (2013.01); *A61K 31/454* (2013.01); *A61K 31/4525* (2013.01); *A61K 31/495* (2013.01); *A61K 31/496* (2013.01)

(58) Field of Classification Search
CPC .................................................. A61K 31/405
USPC ........................................................ 514/419
See application file for complete search history.

(56) References Cited

U.S. PATENT DOCUMENTS

| | | |
|---|---|---|
| 4,658,038 A | 4/1987 | Tamir et al. |
| 6,207,699 B1 | 3/2001 | Rothman |
| 6,340,475 B2 | 1/2002 | Shell et al. |
| 6,635,280 B2 | 10/2003 | Shell et al. |
| 6,723,340 B2 | 4/2004 | Gusler et al. |
| 7,101,912 B2 | 9/2006 | Xiang et al. |
| 7,438,927 B2 | 10/2008 | Berner et al. |
| 7,517,908 B2 * | 4/2009 | Krishnan ............. C12Q 1/6883 514/469 |
| 8,969,400 B2 | 3/2015 | Jacobsen et al. |
| 9,161,911 B2 | 10/2015 | Hou |
| 9,468,627 B2 * | 10/2016 | Jacobsen ................ A61K 45/06 |
| 9,980,903 B2 | 5/2018 | Berner et al. |
| 2006/0013875 A1 | 1/2006 | Han et al. |
| 2012/0258984 A1 | 10/2012 | Sanchez et al. |
| 2013/0338192 A1 | 12/2013 | Krishnan et al. |
| 2016/0375136 A1 * | 12/2016 | Gavin ..................... A23L 33/10 424/729 |

FOREIGN PATENT DOCUMENTS

WO    9107960 A1    6/1991

OTHER PUBLICATIONS

International Search Report and Written Opinion corresponding to PCT/US2019/015391; dated Mar. 22, 2019 (8 pages).
European Search Report corresponding to EP 19743636.3; dated Nov. 24, 2021 (7 pages).
Genazzani, A. R., et al., "Effects of L-5HTP with and without carbidopa on plasma β-endorphin and pain perception possible implications in migraine prophylaxis", Cephalalgia, 6(3), 175-179, 1986.
Russian Office Action corresponding to RU 2020125170; dated Sep. 28, 2020 (5 pages, including English translation).
No Author Listed, "Editorial: Dopa decarboxylase inhibitors", British Medical Journal, 4(5939), 1974, 250-251.
Shenker, Yoram, et al., "Central serotonergic stimulation of aldosterone secretion", The Journal of Clinical Investigation, 76(4), 1985, 1485-1490.
Agren et al. "Low brain uptake of L-[11C]5-hydroxytryptophan in major depression: a positron emission tomography study on patients and healthy volunteers" Acta Psychiatr Scand, 83(6): 449-455 (1991).
Aliño et al. "5-Hydroxytryptophan (5-HTP) and a MAOI (Nialamide) in the Treatment of Depressions. A Double Blind Study" Int Pharmacopsychiatry, 11(1): 8-15 (1976).

(Continued)

*Primary Examiner* — Nizal S Chandrakumar
(74) *Attorney, Agent, or Firm* — Myers Bigel, P.A.

(57) ABSTRACT

Provided are methods of enhancing bioavailability of enterally administered 5-hydroxytryptophan (5-HTP) in a subject in need thereof, said method comprising enterally co-administering low-dose carbidopa with said 5-HTP, as well as pharmaceutical formulations useful for the same. In some embodiments, the 5-HTP and/or low-dose carbidopa are provided as slow-release formulation(s).

22 Claims, 3 Drawing Sheets

(56) References Cited

OTHER PUBLICATIONS

Appleby et al. "A controlled study of fluoxetine and cognitive-behavioural counselling in the treatment of postnatal depression" Bmj, 314(7085): 932-936 (1997).

Asberg, M. "Neurotransmitters and suicidal behavior. The evidence from cerebrospinal fluid studies" Ann. N. Y. Acad Sci, 836: 158-181 (1997).

Badawy et al. "Tryptophan Metabolism m Rat Liver After Administration of Tryptophan, Kynurenine Metabolites, and Kynureninase Inhibitors" Int J Tryptophan Res, 9: 51-65 (2016).

Bartels et al. "Impact of SSRI Therapy on Risk of Conversion From Mild Cognitive Impairment to Alzheimer's Dementia in Individuals With Previous Depression" Am J Psychiatry, 175(3): 232-241 (2018).

Beaulieu et al. "Role of GSKβ in behavioral abnormalities induced by serotonin deficiency" PNAS, 105(4): 1333-1338 (2008).

Blier et al. "Sequential administration of augmentation strategies in treatmerit-resistant obsessive-compulsive disorder: preliminary findings" Int Clin Psychopharmacol, 11(1): 37-44 (1996).

Bowsher et al. "Aromatic L-Amino Acid Decarboxylase: Biochemistry and Functional Significance" In: Boulton A.A., Baker G.B., Yu P.H. (eds) Neurotransmitter Enzymes. Neuromethods (Series 1: Neurochemistry), vol. 5. Humana Press; pp. 33-78 (1986).

Brown et al. "Aggression, suicide, and serotonin: Relationships of CSF amine metabolites" The American Journal of Psychiatry, 139(6): 741-746 (1982).

Bruni et al. "L-5-Hydroxytryptophan treatment of sleep terrors in children" European Journal of Pediatrics, 163(7): 402-407 (2004).

Byerley et al. "5-Hydroxytryptophan: a review of its antidepressant efficacy and adverse effects" J Clin Psychopharmacol, 7(3): 127-137 (1987).

Cangiano et al. "Eating behavior and adherence to dietary prescriptions in obese adult subjects treated with 5-hydroxytryptophan" Am J Clin Nutr 56(5): 863-867 (1992).

Caruso et al. "Double-Blind Study of 5-Hydroxytryptophan versus Placebo in the Treatment of Primary Fibromyalgia Syndrome" The Journal of international medical research 18(3): 201-209 (1990).

Carver et al. "Serotonergic Function, Two-Mode Models of Self-Regulation, and Vulnerability to Depression: What Depression Has in Common With Impulsive Aggression" Psychol Bull, 134(6): 912-943 (2008).

Claxton et al. "A systematic review of the associations between dose regimens and medication compliance" Clinical therapeutics 23(8): 1296-1310 (2001).

Connor et al. "Fluoxetine in post-traumatic stress disorder. Randomised, double-blind study" Br J Psychiatry 175: 17-22 (1999).

Coric et al. "Multicenter, randomized, double-blind, active comparator and placebo-controlled trial of a corticotropin-releasing factor receptor-1 antagonist in generalized anxiety disorder" Depress Anxiety, 27(5): 417-425 (2010).

Da Prada et al. "Inhibition of Decarboxylase and Levels of Dopa and 3-O-Methyldopa: A Comparative Study of Benserazide versus Carbidopa in Rodents and of Madopar Standard versus Madopar HBS in Volunteers" Eur Neurol27(suppl1): 9-20 (1987).

Freitas et al. "Novel Levodopa Formulations for Parkinson's Disease" CNS drugs, 30(11): 1079-1095 (2016).

Fuller et al. "Effect of serotonin-releasing drugs on serum corticosterone concentration in rats" Neuroendocrinology 31(2): 96-100 (1980).

Gasser et al. "Pharmaceutical quality of seven generic Levodopa/Benserazide products compared with original Madopar® / Prolopa®" BMC Pharmacol Toxicol, 14: 24 (2014) (6 pages).

Gershon, M.D. "5-Hydroxytryptamine (serotonin) in the gastrointestinal tract" Curr Opin Endocrinol Diabetes Obes 20(1): 14-21 (2015).

Gijsman et al. "Placebo-Controlled Comparison of Three Dose-Regimens of 5-Hydroxytryptophan Challenge Test in Healthy Volunteers" J Clin Psychopharmacol, 22(2): 183-189 (2002).

Guerdjikova et al. "High-dose escitalopram in the treatment of binge-eating disorder with obesity: a placebo-controlled monotherapy trial" Hum Psychopharmacol 23(1 ): 1-11 (2008).

Hsu et al. "capsule formulation of carbidopa-levodopa (IPX066) with immediate-release carbidopa-levodopa (Sinemet®), sustained-release carbidopa-levodopa (Sinemet® CR), and carbidopa-levodopa-entacapone (Stalevo®)" Journal of clinical pharmacology, 55(9):995-1003 (2015).

Jackson et al. "Pharmacotherapy of Eating Disorders" Nutr Clin Pract, 25(2): 143-159 (2010).

Jacobsen et al. "Adjunctive 5-hydroxytryptophan slow-release for treatment-resistant depression: Clinical and pre-clinical rationale" Trends Pharmacal Sci, 37(11): 933-944 (2016).

Jacobsen et al. "The 5-HT deficiency theory of depression: perspectives from a naturalistic 5-HT deficiency model, the tryptophan hydroxylase 2Arg439His knockin mouse" Philos Trans R Soc Lond B Biol Sci, 367(1601): 2444-2459 (2012a).

Jacobsen et al. "SSRI Augmentation by 5-Hydroxytryptophan Slow Release: Mouse Pharmacodynamic Proof of Concept" Neuropsychopharmacology, 41(9): 2324-2334 (2016b).

Jacobsen et al. "Deficient serotonin neurotransmission and depression-like serotonin biomarker alterations in tryptophan hydroxylase 2 (Tph2) loss-of-function mice" Molecular psychiatry 17(7): 694-704 (2012b).

Kahn et al. "Effect of a serotonin precursor and uptake inhibitor in anxiety disorders: A double-blind comparison of 5-hydroxytryptophan, clomipramine and placebo" Int Clin Psychopharmaco), 2(1): 33-45 (1987).

Lader et al. "Efficacy and tolerability of escitalopram in 12- and 24-week treatment of social anxiety disorder Randomised, double-blind, placebo-controlled, fixed-dose study" Depress Anxiety, 19(4): 241-248 (2004).

Lopes et al. "Overview on gastroretentive drug delivery systems for improving drug bioavailability" Int J Pharm, 510(1): 144-158 (2016).

Lowe et al. "I-5-Hydroxytryptophan augments the neuroendocrine response to a SSRI" Psychoneuroendocrinology, 31(4): 473-484 (2006).

Manegold et al. "Aromatic L-amino acid decarboxylase deficiency: clinical features, drug therapy and follow-up" J Inherit Metab Dis, 32(3): 371-380 (2009).

Mead et al. "Selective serotonin reuptake inhibitors for stroke recovery: a systematic review and meta-analysis" Stroke; a journal of cerebral circulation, 44(3): 844-850 (2013).

Merck (2018). SINEMET® CR. vol. 2018.

Mitra et al. "Feasibility of mini-tablets as a flexible drug delivery tool" Int J Pharm, 525(1): 149-159 (2017).

Nicolodi et al. "L-5-Hydroxytryptophan Can Prevent Nociceptive Disorders in Man" Adv Exp Med Biol, 467: 177-182 (1999).

Nokhodchi et al. "The Role of Oral Controlled Release Matrix Tablets in Drug Delivery Systems" Bioimpacts, 2(4): 175-187 (2012).

Pahwa et al. "Randomized trial of IPX066, carbidopa/levodopa extended release, in early Parkinson's disease" Parkinsonism Relat Disord, 20(2): 142-148 (2014).

Perry et al. "Extracellular 5-hydroxytryptamine concentration in rat hypothalamus after administration of fluoxetine plus L-5-hydroxytryptophan" J Pharm Pharmacol, 45(8): 759-761 (1993).

Rauws et al. "Comparative 90-day toxicity of two decarboxylase inhibitors, benserazide and carbidopa, in the rat" Toxicol Appl Pharmacol, 66(2): 201-220 (1982).

Rose et al. "The effect of carbidopa on plasma and muscle levels of L-dopa, dopamine, and their metabolites following L-dopa administration to rats" Mov Disord, 3(2): 117-125 (1988).

Sargent et al. "Brain 5-HT neurotransmission during paroxetine treatment" The British journal of psychiatry : the journal of mental science, 172:49-52 (1998).

Sharma et al. "To scale or not to scale: the principles of dose extrapolation" Br J Pharmacoll, 57(6): 907-921 (2009).

Shindo et al. "Mechanism of Intestinal Absorption and Brain Uptake of L-5-Hydroxytryptophan in Rats, as compared to Those of L-3,4-Dihydroxyphenylalanine" Chern Pharm Bull (Tokyo), 25(6): 1417-1425 (1977).

Sloan et al. "Fluoxetine as a treatment for emotional lability after brain injury" Brain Inj, 6(4): 315-319 (1992).

(56) References Cited

OTHER PUBLICATIONS

Soulairac et al. "[Effect of 5-hydroxytryptophan, a serotonin precursor, on sleep disorders]" Ann Med Psychol (Paris), 1(5): 792-798 (1977).
Steiner et al. "Fluoxetine in the Treatment of Premenstrual Dysphoria" Canadian Fluoxetine/Premenstrual Dysphoria Collaborative Study Group. N Engl J Med, 332(23): 1529-1534 (1995).
Takahashi et al. Measurement of 5-hydroxyindole compounds during L-5-HTP treatment in depressed patients. Folia Psychiatr Neurol Jpn, 30(4): 463-473 (1976).
Thombre et al. "Osmotic drug delivery using swellable-core technology" J Control Release, 94(1): 75-89 (2004).
Trouillas et al. "Improvement of cerebellar ataxia with levorotatory form of 5-hydroxytryptophan. A double-blind study with quantified data processing" Arch Neurol, 45(11): 1217-1222 (1988).
Turner et al. "Serotonin a la carte: Supplementation with the serotonin precursor 5-hydroxytryptophan" Pharmacol Ther, 109(3): 325-338 (2005).
Turner et al. "Serotonin a la carte: Supplementation with the serotonin precursor 5-hydroxytryptophan" Pharmacol Ther, 109(3): 325-338 (2006).
Van Hiele, LJ. "L-5-Hydroxytryptophan in Depression: the First Substitution Therapy in Psychiatry? The treatment of 99 outpatients with 'therapy-resistant' depressions" Neuropsychobiology, 6(4): 230-240 (1980).
Van Praag, HM. "Serotonin precursors in the treatment of depression" Advances in biochemical psychopharmacology, 34: 259-286 (1982).
Van Woert et al. "Long-term therapy of myoclonus and other neurologic disorders with L-5-hydroxytryptophan and carbidopa" The New England journal of medicine, 296(2): 70-75 (1977).
Veenstra-Vanderweele et al. "Autism gene variant causes hyperserotonemia, serotonin receptor hypersensitivity, social impairment and repetitive behavior" PNAS, 109(14): 5469-5474 (2012).
Verhagen et al. "Gastroretentive carbidopa/levodopa, DM-1992, for the treatment of advanced Parkinson's disease" Mov Disord, 30(9): 1222-1228 (2015).
Viscogliosi et al. "Efficacy and Safety of Citalopram Compared to Atypical Antipsychotics on Agitation in Nursing Home Residents With Alzheimer Dementia" J AmMed Dir Assoc, 18(9): 799-802 (2017).
Westenberg et al. "Kinetics of I-5-hydroxytryptophan in healthy subjects" Psychiatry Res 7(3): 373-385 (1982).
Yeh et al, "Pharmacokinetics and bioavailability of Sinemet CR: a summary of human studies" Neurology, 39(11 Suppl 2): 25-38 (1989).
Yoshimura et al. "Involvement of dopamine in development of hypertension in spontaneously hypertensive rat: effect of carbidopa, inhibitor of peripheral dopa decarboxylase" Clin Exp Hypertens A, 9(10): 1585-1599 (1987).

* cited by examiner

COMPOSITIONS AND METHODS OF ENHANCING 5-HYDROXYTRYPTOPHAN BIOAVAILABILITY

RELATED APPLICATIONS

This application is a 35 U.S.C. § 371 national phase application of International Application Serial No. PCT/US2019/015391, filed Jan. 28, 2019, which claims the benefit of U.S. Provisional Patent Application Ser. Nos. 62/623,073 and 62/743,816, filed Jan. 29, 2018 and Oct. 10, 2018, respectively, the disclosures of which are incorporated by reference herein in their entirety.

STATEMENT OF GOVERNMENT SUPPORT

This invention was made with Government Support under Federal Grant No. 2R01MH079201-06A1 awarded by the NIH. The Government has certain rights to this invention.

BACKGROUND 5-hydroxytryptophan (5-HTP) is the natural immediate precursor of serotonin (aka, 5-hydroxytryptamine, 5-HT). 5-HTP has been reported to have therapeutic potential in a range of disorders related to central nervous system function (Turner et al, 2006a), but exhibits in humans fast absorption ($T_{Max}$~1 h) and rapid elimination ($T_{1/2}$~2 h) (Gijsman et al, 2002; Westenberg et al, 1982). 5-HTP as a molecule alone may be ill-suited for drug therapy, because of fast-onset $C_{Max}$-related adverse events upon dosing, and because of a need to dose 4-6 times per day to maintain reasonably stable 5-HTP exposure, a dosing requirement that is unrealistic and impractical in a general therapeutic setting (Jacobsen et al, 2016a).

Carbidopa and benserazide are peripheral inhibitors (PDI) of the aromatic amino acid decarboxylase enzyme (AAAD). In humans, PDI co-treatment has been used to enhance the bioavailability of the dopamine precursor levodopa for Parkinson's disease therapy (Freitas et al, 2016), and of the 5-HT precursor 5-HTP for experimental therapeutic purposes (Turner et al, 2006b). For 5-HTP, PDI co-treatment may also reduce human gastrointestinal (GI) adverse events—e.g. nausea, diarrhea, upset stomach, vomiting—related to conversion of 5-HTP to 5-HT in the GI tract (Byerley et al, 1987).

Both benserazide and carbidopa are usually used with levodopa in a levodopa:PDI ratio of 4:1 (Merck, 2017; Roche, 2015). However, benserazide is a more potent PDI inhibitor than carbidopa. For example, after oral administration benserazide is a 10-fold more potent inhibitor of AAAD in the peripheral organs than is carbidopa (Da Prada et al, 1987). Consequently, the starting dose of benserazide is around half that of carbidopa (Merck, 2017; Roche, 2015), and benserazide and carbidopa cannot be dose-substituted on a simple basis.

Reports using a PDI, mostly carbidopa, together with 5-HTP m human chronic studies have used doses of PDI ranging from 150 mg/day to 1000 mg/day. Such PDI doses will cause robust systemic inhibition of AAAD in all peripheral tissues (i.e., all tissues outside the brain). The reported 5-HTP:PDI ratio is usually between 4:1 and 10:1, similar to that of when a PDI is used with levodopa to treat Parkinson's disease. Previous chronic clinical studies with oral 5-HTP and PDI treatment used doses of PDI >2 mg/kg/day (given a 70 kg patient body weight), which will cause robust inhibition of AAAD in all systemic peripheral tissues. Reported human chronic studies with carbidopa and 5-HTP (e.g., Kahn and Westerberg, 1985; van Hiele, 1980; van Praag, 1982) will have produced average carbidopa plasma levels >25 ng/ml (Verhagen Metman et al, 2015; Yeh et al, 1989), by extrapolating across the references here cited.

When PDIs are given in systemically active doses, e.g. carbidopa 1-2 mg/kg/day, together with levodopa to mortally ill Parkinson's patients, no adverse effects have been possible to ascribe specifically to PDI treatment, as it is difficult to separate the effects when the PDI and levodopa are administered together. The safety profile of PDI therapy in the absence of levodopa is further difficult to assess as PDI treatment's action on peripheral dopamine, adrenaline, and noradrenaline (inhibits synthesis) will be off-set by the concomitant levodopa administration (enhances synthesis) (Rose et al, 1988).

PDIs are not specific inhibitors of AAAD; they can also inhibit enzymes of the kynurenine pathway, anomalies of which are associated with CNS, metabolic, and immune disorders (Badawy and Bano, 2016). Further, in animals chronic PDI treatment, i.e., carbidopa, benserazide, without levodopa can cause significant toxic effects, including kidney insufficiency and growth anomalies (Rauws et al, 1982; Yoshimura et al, 1987). Moreover, in humans, congenital amino acid decarboxylase deficiency causes serious autonomic, movement, and other symptoms, indicating that long-term PDI treatment could potentially have broad-spectrum toxic effects (Manegold et al, 2009).

Altogether, the long-term safety of PDI treatment without levodopa treatment in otherwise healthy humans has not been established, and the pharmacology of PDIs holds risk for negative effects on a variety of physiological systems in the periphery. Hence, human therapy with 5-HTP and a lower dose of PDI, such as carbidopa, if possible, would be preferable.

SUMMARY

As demonstrated in the accompanying figures, it has been unexpectedly found that low-dose carbidopa, particularly in a high 5-HTP:PDI ratio, can substantially (>100%) enhance 5-HTP oral bioavailability, without causing systemic carbidopa plasma levels in the therapeutically active range.

Thus, one aspect of the present disclosure provides a method of enhancing the bioavailability of 5-HTP in a subject (e.g. human subject) comprising, consisting of, or consisting essentially of co-administering to the subject a therapeutically effective amount of 5-HTP and a low-dose of carbidopa to the subject, thereby enhancing 5-HTP bioavailability in the subject.

In some embodiments, the low-dose carbidopa produces sub-clinical carbidopa plasma levels, which causes the carbidopa to act only locally in the intestinal tract to enhance 5-HTP bioavailability, which, in turn, minimizes the risk of toxicity and other undesirable physiological effects related to systemic carbidopa exposure.

In some embodiments, a method of enhancing bioavailability of enterally administered 5-HTP in a human subject in need thereof includes: enterally co-administering low-dose carbidopa with said 5-HTP, said low-dose carbidopa provided in a daily dosage of from about 0.1 or 0.2 to about 0.5, 0.6 or 0.8 mg/kg/day (or about 5 or 10 mg to about 35, 50 or 60 mg per day) to thereby enhance the bioavailability of the enterally administered 5-HTP. In some embodiments, the 5-HTP and carbidopa are administered in a daily dosage ratio of from 100:1, 80:1, 60:1, or 50:1, to 40:1, 30:1 or 20:1 of 5-HTP:carbidopa.

In some embodiments, upon enterally co-administering the low-dose carbidopa, the subject has blood plasma levels of carbidopa of less than 25, 20, 15, 10, 5, or 2 ng/ml.

In some embodiments, the 5-HTP and low-dose carbidopa are administered once, twice, or three times per day.

In some embodiments, the formulation is administered in a manner selected from the group consisting of oral immediate-release formulation, an oral slow-release formulation, an oral intra-intestinal gel, a rectal suppository, and combinations thereof.

In some embodiments, 5-HTP and carbidopa are provided as a slow-release (SR) formulation of the 5-HTP and the low-dose carbidopa, in the same or separate dosage forms.

In some embodiments, the subject is in need of treatment for a psychiatric disorders and/or neurologic disorders, such as mood anomalies or anomalies in impulse or aggression control. In some embodiments, the subject is in need of treatment for depression, social anxiety, panic disorder, generalized anxiety disorder, OCD, impulse control disorders, suicidality, borderline personality disorder, fibromyalgia, ataxia, mood, cognitive, or behavioral symptoms and agitation related to neurological disorders (e.g. Alzheimer's, Parkinson's), stroke recovery, autism, migraine, sleep disorders, premenstrual dysphoria, post-traumatic stress disorder, post-partum depression, or depression after interferon treatment. In some embodiments, the subject is in need of treatment for depression, anxiety, suicidality, obsessive compulsive disorder, or ADHD. In some embodiments, the subject is in need of treatment for depression, major depressive disorder or treatment-resistant depression (not full remission after treatment with a serotonin reuptake inhibitor).

In some embodiments, the method comprises monotherapy with the 5-HTP and low-dose carbidopa. In some embodiments, the method comprises adjunctive therapy with the 5-HTP and low-dose carbidopa along with a serotonin enhancer. In some embodiments, the serotonin enhancer is selected from the group consisting of serotonin reuptake inhibitors, serotonin norepinephrine reuptake inhibitors, triple-reuptake inhibitors, monoamine oxidase inhibitors, tricyclic antidepressants, serotonin agonists, amphetamines, serotonin precursors, serotonin prodrugs, intermediates in the biosynthesis of serotonin, and pharmaceutically acceptable salts thereof. In some embodiments, the serotonin enhancer is a selective serotonin reuptake inhibitor (SSRI). In some embodiments, the serotonin enhancer is selected from the group consisting of: citalopram, dapoxetine, escitalopram, fluoxetine, fluvoxamine, indalpine, paroxetine, sertraline, vilazodone, vortioxetine, zimelidine and combinations thereof. In some embodiments, the 5-HTP and low-dose carbidopa are administered orally, optionally in the same or separate dosage forms.

In some embodiments, the low-dose carbidopa provided in a daily dosage of from about 0.1 or 0.2 to about 0.5 mg/kg/day (or about 5 or 10 mg to about 35 mg per day).

In some embodiments, the 5-HTP is provided in a daily dosage of from about 0.1, 0.2, 0.5, or 0.75, to about 1, 4, or 6 grams per day.

Also provided is a pharmaceutical formulation or kit of parts suitable for enteric administration comprising 5-HTP and low-dose carbidopa, said formulation suitable for once, twice or three times daily administration.

In some embodiments, the low-dose carbidopa in the pharmaceutical formulation or kit of parts is provided in a daily dosage of from about 0.1 or 0.2 to about 0.5, 0.6 or 0.8 mg/kg/day (or about 5 or 10 mg to about 35, 50 or 60 mg per day).

In some embodiments, the 5-HTP and low-dose carbidopa are provided in the pharmaceutical formulation or kit of parts at a dosage ratio of from 100:1, 80:1, 60:1, or 50:1, to 40:1, 30:1 or 20:1 of 5-HTP:carbidopa.

In some embodiments, the formulation is a solid dosage form suitable for oral or rectal administration.

In some embodiments, the formulation of 5-HTP and/or carbidopa is one tablet, capsule, or other formulation for daily dosing; or two tablets, capsules, or other formulation for twice-daily dosing.

In some embodiments, the formulation comprises a slow-release formulation of 5-HTP and/or carbidopa. In some embodiments, the slow-release formulation comprises a gastroretentive formulation. In some embodiments, the 5-HTP and low-dose carbidopa are co-administered with a meal (e.g., when provided as a gastroretentive formulation).

Also provided is the use of a low-dose carbidopa as taught herein in a method of enhancing the bioavailability of 5-HTP in a subject (e.g. human subject) comprising, consisting of, or consisting essentially of co-administering to the subject a low-dose of carbidopa with the 5-HTP, thereby enhancing 5-HTP bioavailability in the subject.

Further provided is the use of a low-dose carbidopa as taught herein in a method of preparing a medicament for enhancing the bioavailability of 5-HTP in a subject (e.g. human subject).

The foregoing aspects and other features of the disclosure are explained in the following description, taken in connection with the accompanying drawings.

BRIEF DESCRIPTION OF THE DRAWINGS

FIG. 1. Effects of low-dose carbidopa on the 5-HTP plasma elevation induced by 5-HTP administration. Carbidopa dose-dependently augmented the 5-HTP plasma elevation. The effect was similar in WT and 5-$HT_{Hypo}$ mice (mice with selective and partial brain 5-HT deficiency due to a mutation in tryptophan hydroxylase (Beaulieu et al, 2008)), likely reflecting that the two genotypes of mice had similar 5-HTP plasma levels at baseline. * denotes a statistically significant difference from the group only treated with 5-HTP 200 mg/kg/day. One-way ANOVA, Dunnett's post-hoc test.

FIG. 4A-4D. HPLC electrochemical quantification of carbidopa in plasma.

FIG. 5A-5C. Qualitative illustration of the mechanism of action of the present invention. Under baseline conditions (FIG. 5A), essentially no 5-HTP is present in the systemic circulation. (At baseline brain 5-HT is synthesized locally in the brain from tryptophan) 5-HTP treatment alone (FIG. 5B) will moderately elevate 5-HTP in the systemic circulation, and moderately elevate brain 5-HT. Co-treatment with low-dose carbidopa (FIG. 5C) will significantly inhibit amino acid decarboxylase locally in the intestine, reducing first-pass metabolism of 5-HTP, allowing more 5-HTP to enter the systemic circulation and to cause a stronger elevation of brain 5-HT after 5-HTP treatment compared to after treatment with 5-HTP alone. Simultaneously, in the systemic circulation the carbidopa levels will be too dilute to functionally inhibit AAAD. Symbols: •, carbidopa. ♦, 5-HTP.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including", "comprising," or "having," and variations thereof, is meant to encompass the elements listed thereafter and equivalents thereof as well as additional elements. Embodiments recited as "including", "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

I. 5-Hydroxytryptophan

"5-hydroxytryptophan" or "5-HTP" is the precursor of serotonin (aka 5-hydroxytryptamine, 5-HT) in the body. In the human body, 5-HTP is synthesized from dietary tryptophan by tryptophan hydroxylase (subtype 1 in the periphery, subtype 2 in most neurons) (Jacobsen et al, 2016a). 5-HTP is rapidly converted to 5-HT by aromatic amino acid decarboxylase (AAAD), a high-capacity ubiquitously expressed enzyme that is unsaturated under baseline conditions (Bowsher, 1986). 5-HTP is thus the natural, immediate, and rate-limiting precursor of 5-HT.

Exogenously administered 5-HTP, whether orally or parenterally, elevates brain 5-HT synthesis and functional levels (i.e., extracellular 5-HT, 5-HT$_{Ext}$) in animal models (Jacobsen et al, 2016b; Perry and Fuller, 1993) as well as in humans (Agren et al, 1991; Sargent et al, 1998).

As is generally the case with the 5-HT system, 5-HTP biology and pharmacology appear very similar between non-human mammalian species, e.g. rodents, and humans.

For instance, in both rodents and humans, 5-HTP's sole known metabolic fate is conversion to 5-HT, by AAAD (Jacobsen et al, 2016a); at baseline, 5-HTP plasma and tissue levels are very low (Gijsman et al, 2002; Jacobsen et al, 2016b); and exogenous 5-HTP alone only modestly elevates neuroendocrine biomarkers of brain 5-HT function, while exogenous 5-HTP strongly synergizes with concomitant SSRI administration to elevate 5-HT function beyond the effect of the SSRI (Fuller and Snoddy, 1980; Sargent et al, 1998). Therefore, findings on 5-HTP pharmacology in rodents translate well to the human.

5-HTP can be readily sourced from the seeds of the plant *Griffonia Simplicifolia* and is available commercially. 5-HTP can also be obtained via chemical synthesis (see, e.g. CN103554005A). Exogenous administration of 5-HTP has been reported in experimental human trials to have therapeutic potential in a range of disorders, for instance depression as monotherapy (Takahashi et al, 1976), depression as adjunctive therapy (van Praag, 1982), anxiety (Kahn et al, 1987), obesity (Cangiano et al, 1992), ataxia (Trouillas et al, 1988), migraine (Nicolodi and Sicuteri, 1999), fibromyalgia (Caruso et al, 1990), insomnia (Soulairac and Lambinet, 1977), and sleep terrors (Bruni et al, 2004).

Further, 5-HTP as a monotherapy or adjunctive therapy will enhance 5-HT function in the brain, and 5-HTP could treat additional disorders, as monotherapy or adjunctive therapy, known to be treatable by 5-HT stimulatory drugs, including, but not limited to, post-traumatic stress disorder (Connor et al, 1999), social phobia (Lader et al, 2004), anxiety disorders (Coric et al, 2010), Alzheimer's agitation (Viscogliosi et al, 2017), Alzheimer's related dementia (Bartels et al, 2018), obsessive compulsive disorder (Blier and Bergeron, 1996), premenstrual dysphoria (Steiner et al, 1995), post-partum depression (Appleby et al, 1997), bulimia (Jackson et al, 2010), binge-eating disorder (Guerdjikova et al, 2008), stroke recovery (Mead et al, 2013), and/or pseudobulbar affect (Sloan et al, 1992). Further, a 5-HTP drug product could treat disorders whose pathology is believed to involve 5-HT deficiency, including but not limited to, impulse control disorders (Carver et al, 2008), borderline personality disorder (Brown et al, 1982), suicidality (Asberg, 1997), and/or autism (Veenstra-VanderWeele et al, 2012).

After oral administration, 5-HTP is rapidly absorbed from the upper intestine ($T_{Max}$~1 h) and then rapidly eliminated (converted to 5-HT) with a half-life of ~2 h (Gijsman et al, 2002; Westenberg et al, 1982). The rapid absorption is associated with $C_{Max}$-related gastrointestinal (GI) adverse events, such as nausea, diarrhea, abdominal pain, and vomiting (Byerley et al, 1987; Lowe et al, 2006). These undesirable adverse events are caused by unintended conversion of 5-HTP to 5-HT in the GI (Turner et al, 2006b). In fact, animal studies suggest that more than 50% of exogenously administered 5-HTP is converted to 5-HT during transport over the intestinal wall (Shindo et al, 1977). 5-HT promotes GI motility, fluid secretion, and pain sensation (Gershon, 2013), which corresponds to the observed GI adverse events associated with 5-HTP administration (Turner et al, 2006b). To reduce 5-HTP-induced GI adverse events, the 5-HTP dose in most trials had to be titrated up in multiple dose steps over multiple days or weeks (Alino et al, 1976; van Hiele, 1980; van Praag, 1982). This unfortunately complicates therapy, compromises adherence, and impairs overall clinical effectiveness (Claxton et al, 2001). Altogether, 5-HTP's rapid pharmacokinetics makes 5-HTP in its native immediate release form difficult to use as a therapeutic. Indeed, there currently are no Food and Drug Administration approved drug products using 5-HTP as an active moiety.

5-HTP's short half-life necessitates multiple, i.e., 4-6, daily doses, to maintain reasonably stable 5-HTP plasma exposure (Jacobsen et al, 2016a; van Praag, 1982). Such a regimen is impractical in a real-life therapeutic setting. Adherence will be low and the therapeutic effectiveness compromised. Fortunately, slow-release (SR) delivery can markedly and to an unexpected degree enhance the drug properties of 5-HTP (see U.S. Pat. Nos. 9,468,627 and 8,969,400 to Jacobsen et al), which is supported by animal data (Jacobsen et al, 2016b). Further, 5-HTP's oral bioavailability appears to be modest (Gijsman et al, 2002). Therapeutic studies often employ high daily doses of 5-HTP when native 5-HTP is given alone, e.g. 900 mg/day for obesity (Cangiano et al, 1992). High 5-HTP doses pose a disadvantage because of large size of the solid dosage form and/or multiple tablets or capsules per dose.

As used herein, "slow-release formulation of 5-HTP" refers to a formulation with the ability to release 5-HTP at a slow rate, such that the plasma $T_{1/2}$ is increased and/or $T_{Max}$ is delayed as compared to an immediate release formulation. The terms "5-HTP at a slow rate" and "5-HTP at a slow release" are used interchangeably and refer to the ability to cause the 5-HTP to be released in the subject at a slower rate than if administered directly. See U.S. Pat. No. 9,468,627 to Jacobsen et al., which is incorporated by reference herein in its entirety. Other terms that may be used for such formulations include, but are not limited to, "sustained-release," "controlled-release," "extended-release," and "time-release."

For example, immediate-release oral 5-HTP typically has a $T_{1/2}$ of about 2 hours, and thus a slow-release 5-HTP would have a $T_{1/2}$ greater than 3, 4, 5, 6 or 7 hours. In some embodiments, the $T_{1/2}$ is at least 8 hours. In some embodiments, the $T_{1/2}$ is from 8, 10 or 12 hours to 24, 48 or 72 hours.

As another example, immediate-release oral 5-HTP has a $T_{Max}$ of 1-2 hours. Thus, in some embodiments, the slow-release formulation of 5-HTP is administered and/or formulated such that the $T_m$ (time of maximal plasma concentration after administration) of 5-HTP is at least 2 hours, or between 2 hours and 12 hours.

In some embodiments, 5-HTP is provided in a therapeutically effective amount in a formulation suitable for enteric administration. As used herein, the term "therapeutically effective amount" refers to the amount of 5-HTP that is sufficient to show a benefit in the subject. In some embodiments, the formulation is provided in a unit dose for once-daily or twice-daily use. See U.S. Pat. No. 8,969,400 to Jacobsen et al., which is incorporated by reference herein in its entirety.

In some embodiments, a daily dose of 0.05 to 10 grams of 5-HTP may be provided (e.g., as one tablet, capsule, or other dosage formulation for daily dosing, or two tablets, capsule, or other formulation for twice-daily dosing with half the daily dosage in each). In some embodiments, the daily dose may be from 0.01, 0.05, 0.1, 0.2, 0.5, or 0.75, to 5, 8, or 10 grams per day. In some embodiments, the daily dose may be from 1 to 5 grams per day. In some embodiments, the daily dose may be from 1 to 3 grams per day.

In some embodiments, 5-HTP is provided in a daily dosage of from about 0.1, 0.2, 0.5, or 0.75 grams per day, to about 1, 4, or 6 grams per day, for a human subject. In some embodiments, 5-HTP is administered so as to achieve plasma 5-HTP levels averaging 10-100 ng/ml. In some embodiments, 5-HTP is administered so as to achieve plasma 5-HTP levels averaging 100-1000 ng/ml. In some embodiments, 5-HTP is administered so as to achieve plasma 5-HTP levels averaging 1000-10000 ng/ml.

II. Low-Dose Carbidopa

Carbidopa inhibits aromatic amino acid decarboxylase (AAAD), the enzyme catalyzing the conversion of 5-HTP to 5-HT, the conversion of levodopa to dopamine, and other similar metabolic reactions (Bowsher R. R., 1986). Therapeutic maintenance doses of carbidopa are >1 mg/kg/day (assuming a patient body weight of 70 kg) (Merck, 2017; Pahwa et al, 2014; van Praag, 1982). At steady state, in a therapeutic scenario, average plasma levels of carbidopa at maintenance doses are ≥25 ng/ml (range: 25-150 ng/ml) (Verhagen Metman et al, 2015; Yeh et al, 1989).

"Low-dose" carbidopa as used herein refers to a dosage below that normally used clinically. AAAD, being the enzyme catalyzing the conversion of 5-HTP to 5-HT, is present in large excess and is unsaturated under baseline conditions (Bowsher R. R., 1986). As a consequence, under baseline conditions 5-HTP levels are very low, reflecting that the rate-limiting step in 5-HT synthesis is formation of 5-HTP from tryptophan, catalyzed by tryptophan hydroxylase (Jacobsen et al, 2012a). It follows that minimal levels of a PDI (e.g. average carbidopa <25 ng/ml (Verhagen Metman et al, 2015; Yeh et al, 1989)) will have no substantial impact on AAAD activity in the systemic circulation and internal organs.

In some embodiments, low-dose carbidopa is provided in a daily dosage of from about 0.1 or 0.2 to about 0.5, 0.6 or 0.8 mg/kg/day (or about 5 or 10 mg to about 35, 50 or 60 mg per day) for a human subject.

Figure 5A:
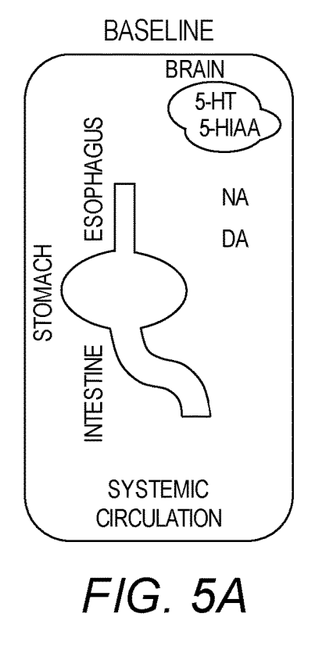
Figure 5B:
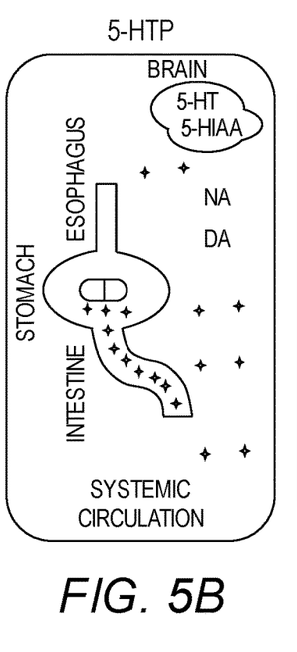
Figure 5C:
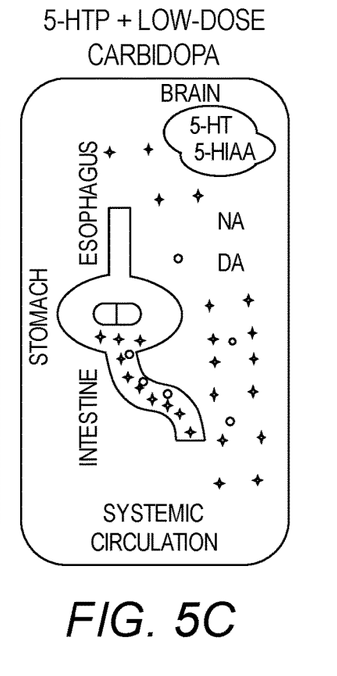

In some embodiments, the 5-HTP and low-dose carbidopa co-administration/dosage form functions in such a way that 5-HTP conversion to 5-HT is inhibited substantially only in the intestine, at the site of 5-HTP absorption, while AAAD activity in the systemic circulation, internal organs, and brain will remain substantially and functionally uninhibited (see FIG. 5A-5C).

Without wishing to be bound by theory, the selective inhibition of AAAD in the intestine with low-dose carbidopa as taught herein protects 5-HTP, wholly or partly, from AAAD catalyzed conversion to 5-HT in the intestine. In turn, this allows more 5-HTP to enter the systemic blood circulation and to be transported to the brain where the 5-HTP can be converted to 5-HT and augment brain 5-HT synthesis and 5-HT function. Further, as most adverse events from 5-HTP arises from conversion to 5-HT in the intestine (e.g. diarrhea, nausea, GI discomfort, vomiting) (Byerley et al, 1987), the present invention will have the potential to reduce such 5-HT-related GI adverse events.

The enhanced 5-HT function in the brain may manifest as increased net 5-HT synaptic and extra-synaptic release and elevated levels of extracellular 5-HT (5-$HT_{Ext}$). This causes increased 5-HT neurotransmission through serotonin receptors in the brain, an action which can exert a therapeutic effect. Downstream mechanisms of serotonin receptors include, but are not limited to, neural plasticity, electrophysiological changes, modulations in brain connectivity, alterations in brain structural circuitry, alterations in brain functional circuitry, alterations in gross brain structure, alterations in neurite structure and complement, alterations in neurotrophic factors, alterations in neurogenesis, alterations in neuron number and complement, alterations in non-neuron cell number and complement, and alterations in apoptosis. In some embodiments, the co-administration may further comprise administration of another serotonergic therapeutic.

As used herein, "slow-release formulation of carbidopa" refers to a formulation with the ability to release the low-dose carbidopa at a slow rate, such that the plasma $T_{1/2}$ is delayed and/or $T_{Max}$ is decreased as compared to an immediate release formulation. The slow-release formulation of carbidopa can be provided together with 5-HTP in the same dosage form, or in separate dosage forms. The terms "carbidopa at a slow rate" and "carbidopa at a slow release" are used interchangeably and refer to the ability to cause the carbidopa to be released in the subject at a slower rate than if administered directly, in an immediate release dosage form. See, e.g., U.S. 2006/0013875 to Han et al. (Pahwa et al, 2014). Other terms that may be used for such formulations include, but are not limited to, "sustained-release," "controlled-release," "extended-release," and "time-release."

III. Formulations and Administration

The 5-HTP and/or carbidopa used in the invention can be the free base; a salt; a conjugate (e.g. an amino acid conjugate, a hydrocarbon conjugate, a lipid conjugate); a conjugate to alter the absorption, distribution, metabolism, and/or excretion properties; or an isotopic modification to alter the absorption, distribution, metabolism, and/or excretion properties. See U.S. Pat. No. 4,658,038 to Tamir et al.; U.S. Pat. No. 7,101,912 to Xiang et al.; U.S. Pat. No. 8,969,400 to Jacobsen et al., which are incorporated by reference herein.

Solid pharmaceutical dosage forms suitable for enteric administration of 5-HTP and/or carbidopa can include tablets, capsules, or particulates that can be prepared using standard pharmaceutical approaches for making drug formulations known to the person skilled in the art. Examples includes, but are not limited to, gastroretentive formulations (Lopes et al, 2016), swellable matrix tablets (Verhagen Metman et al, 2015), erosible matrix tablets (Nokhodchi et al, 2012), osmotic tablets (Thombre et al, 2004), mini-tablets (Mitra et al, 2017), and micro-beads (Freitas et al, 2016).

In some embodiments, the formulation is a slow-release gastroretentive formulation of 5-HTP and low-dose carbidopa, either in the same or separate dosage forms for co-administration (see review, Lopes et al, 2016; see also U.S. Pat. Nos. 6,340,475; 6,635,280; 6,723340, 9,161,911; and 9,980903).

The 5-HTP and/or carbidopa dosage forms can be administered with or without food, depending on the specific embodiment. In some embodiments, the dosage form(s) are to be taken/administered with food (e.g. with a meal; see U.S. Pat. No. 7,438,927). In other embodiments, the dosage form(s) are to be taken/administered while fasting.

The solid dosage form suitable for enteric administration can deliver 5-HTP and/or carbidopa either predominantly to the stomach, jejunum, ileum, colon, or rectum, or to combinations thereof. The 5-HTP and/or carbidopa can be released via the solid dosage over a period, ranging from essentially instantaneously at the site(s) of delivery to up 24 h, as is appropriate for the indication in question. The 5-HTP and/or carbidopa dosage form can also be a liquid, gel, or semi-solid, or such non-solids incorporating solid elements.

In some embodiments, enteric dosage forms can be administered orally or rectally. Doses can be administered once, twice, or more frequent, as required for therapy. One or more units can be administered at each dose. The 5-HTP and/or carbidopa dosage form can be administered acute, over one day, several days, several weeks, several months, or indeterminate, depending on the therapeutic need of the subject being treated.

In some embodiments, each sub-dose (e.g. first out of a total of two or more daily administrations) encompasses one tablet capsule, or other dosage form. In other embodiments, each sub-dose includes two or more tablets, capsules, or other dosage forms.

The 5-HTP and/or carbidopa dose can be titrated up to the final dose over several days, weeks, or months, or the final dosage strength can be administered from the start of treatment.

The 5-HTP and carbidopa co-administration can be used therapeutically as monotherapy, i.e., with no other concomitant serotonin enhancer therapies. Alternatively, the 5-HTP and carbidopa co-administration can be used therapeutically as adjunctive therapy, i.e., together with another serotonergic therapy or serotonin enhancer, including, but not limited to, serotonin reuptake inhibitors, serotonin norepinephrine reuptake inhibitors, monoamine oxidase inhibitors, serotonin agonists, serotonin antagonists, serotonin receptor allosteric modulators, serotonin precursors, serotonin synthesis co-factors, and/or modulators of biological elements in serotonin metabolic pathway. See U.S. Pat. No. 9,468,627 to Jacobsen et al.

"Serotonin enhancer" as used herein refers to any compound that increases, directly or indirectly, the availability of serotonin in the central nervous system for binding to serotonin receptors at the post-synaptic membrane, or directly stimulates serotonin receptors, and includes, but is not limited to, serotonin reuptake inhibitors, monoamine oxidase inhibitors, tricyclic antidepressants, serotonin agonists, amphetamines, serotonin precursors, serotonin prodrugs, intermediates in the biosynthesis of serotonin, co-factors, and pharmaceutically acceptable salts thereof. Such compounds may be given alone or in combination with other serotonin enhancers.

The term "SSRI" or "selective serotonin reuptake inhibitor" refers to those compounds typically used as antidepressants and are associated with the increase in the extracellular level of the neurotransmitter serotonin by inhibiting its uptake into the presynaptic cell, increasing the level of serotonin in the synaptic cleft available to bind to post-synaptic serotonin receptors. Examples of suitable SSRIs include, but are not limited to, citalopram, dapoxetine, escitalopram, fluoxetine, fluvoxamine, indalpine, paroxetine, sertraline, vilazodone, vortioxetine, zimelidine, and combinations thereof.

The 5-HTP and low-dose carbidopa may be provided together in the same dosage form, or they may be provided separately as a kit of parts comprising separate dosage forms that may be subsequently brought together for use in conjunction with each other in combination therapy as taught herein. They may also be packaged and presented together as separate component(s) of a kit of parts in adjunctive therapy with a serotonin enhancer (e.g., SSRI).

The following non-limiting Examples are provided to further describe and demonstrate the present invention.

EXAMPLES

Methods

Mice: Adult mice were used, both wildtype (WT) mice with normal 5-HT levels and '5-$HT_{Hypo}$' mice with reduced brain 5-HT synthesis and levels (Beaulieu et al, 2008). The 5-$HT_{Hypo}$ mice are a naturalistic model of brain 5-HT deficiency, which is known to be a pathogenic factor in several CNS disorders, e.g. depression and suicide.

Drug treatments: Carbidopa was used as a PDI. To model oral drug delivery occurring in humans during a therapeutic scenario, 5-HTP and carbidopa was delivered via the mouse food (standard chow). This approach distributed the drug delivery over time, imparting a measure of 'slow-release' (aka sustained-, extended-, time-, controlled-release) delivery. 5-HTP was administered in a dose of 200 mg/kg/day. Carbidopa was administered in doses of 2, 5 or 10 mg/kg/day in addition to 5-HTP, to assess the effect of carbidopa on the outcomes of 5-HTP treatment. To assess the effect of carbidopa alone, groups of mice were also administered carbidopa 10 mg/kg/day, the highest carbidopa dose, without concomitant 5-HTP. Comparisons were made to untreated mice. Duration of all treatments was 14 days, which is considered chronic in mouse experiments.

Sample collection: During treatments blood samples were collected to assess plasma levels of 5-HTP and carbidopa. At end of treatments mice were euthanized and brain tissues (frontal cortex) were collected.

Figure 4A:
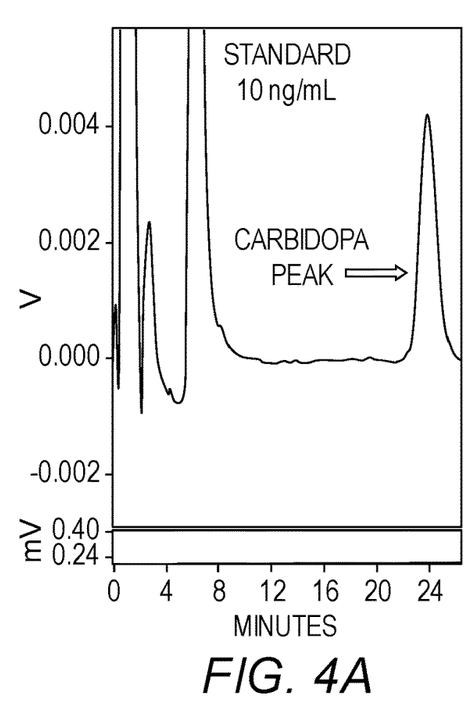
FIG. 4A: 10 ng/ml standard in perchloric acid. Carbidopa peak visible at 24 min.
Figure 4B:
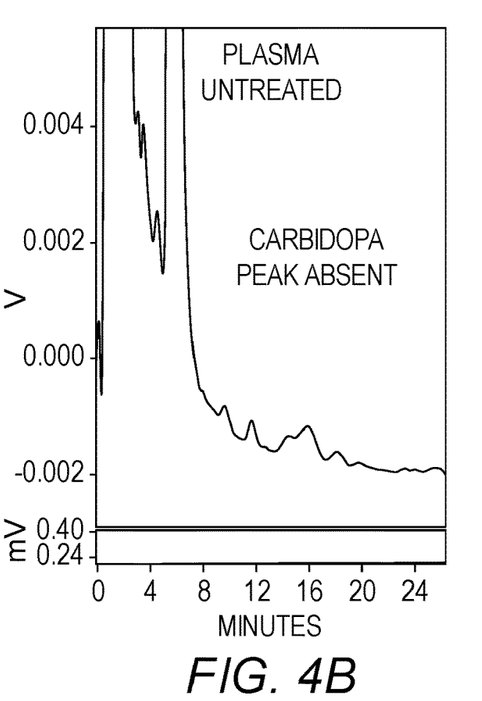
FIG. 4B: Plasma extract from mouse not treated with carbidopa. No carbidopa peak visible. Baseline undulations at 24 min is detector noise.
Figure 4C:
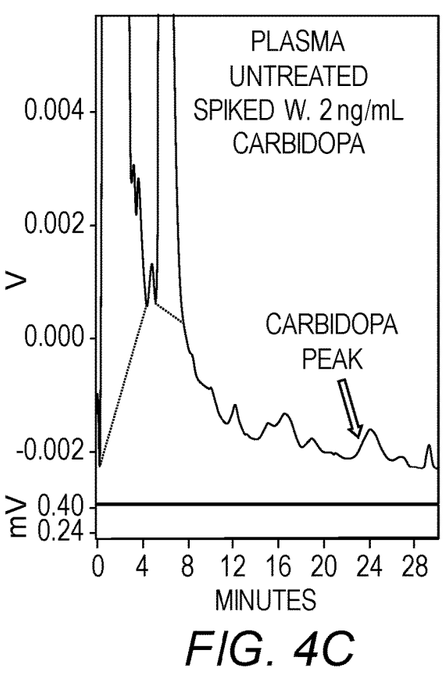
FIG. 4C: Plasma extract from a mouse not treated with carbidopa, but the plasma spiked with carbidopa to a concentration of 2 ng/ml prior to extraction. Carbidopa peak visible at 24 min.
Figure 4D:
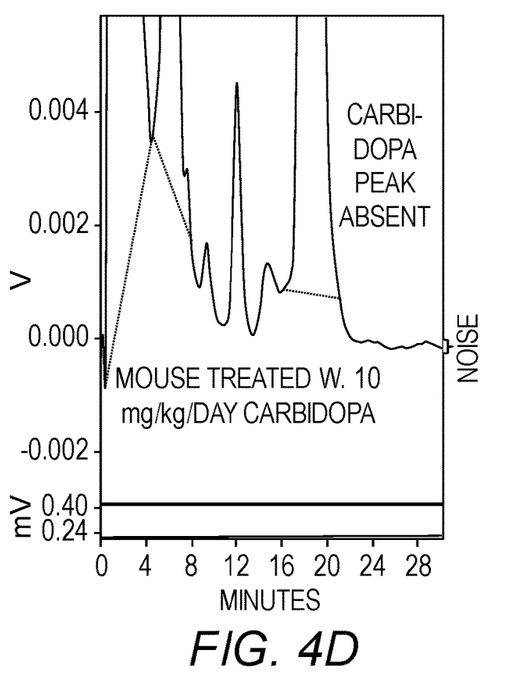
FIG. 4D: Plasma extract from mouse treated with 10 mg/kg/day carbidopa. No carbidopa peak visible. Baseline undulations at 24 min is detector noise, as indicated.

Quantitative analysis: Levels of plasma 5-HTP, plasma carbidopa, brain 5-HT, and brain 5-hydroxyindoleacetic acid (5-HIAA, major 5-HT metabolite) were quantified using HPLC, as described (Jacobsen et al, 2012b). The limits of detection for 5-HT and 5-HTP in plasma were 1 ng/ml and for carbidopa in plasma 2 ng/ml (FIG. 4C).

Results & Discussion

Figure 1:
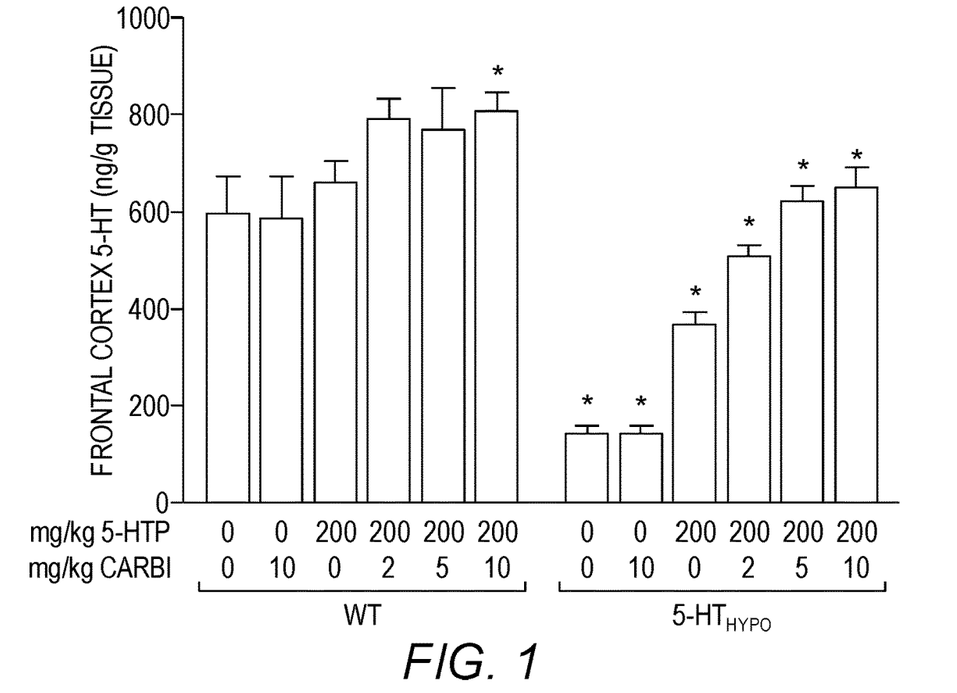
Figure 2:
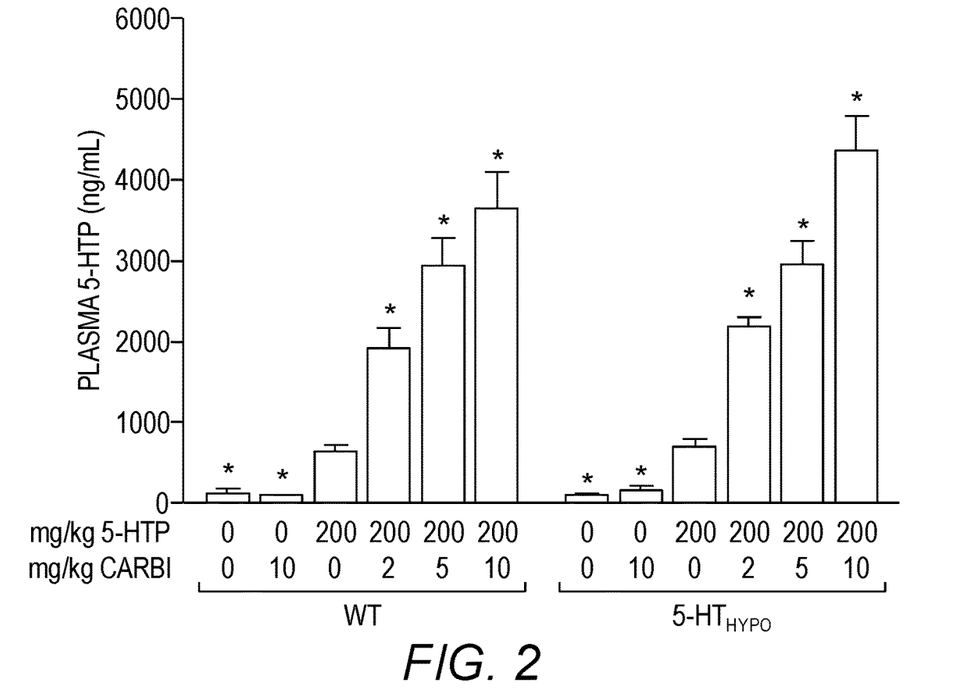
FIG. 2. Effects of low-dose carbidopa on the brain 5-HT tissue elevation induced by 5-HTP administration. Carbidopa dose-dependently augmented the 5-HT tissue elevation induced by 5-HTP. The effect was proportionally more pronounced in 5-$HT_{Hypo}$ mice, which due do their lower endogenous brain 5-HT synthesis had lower brain 5-HT levels at baseline. * denotes a statistically significant difference from the group only treated with 5-HTP 200 mg/kg/day. One-way ANOVA, Dunnett's post-hoc test.
Figure 3:
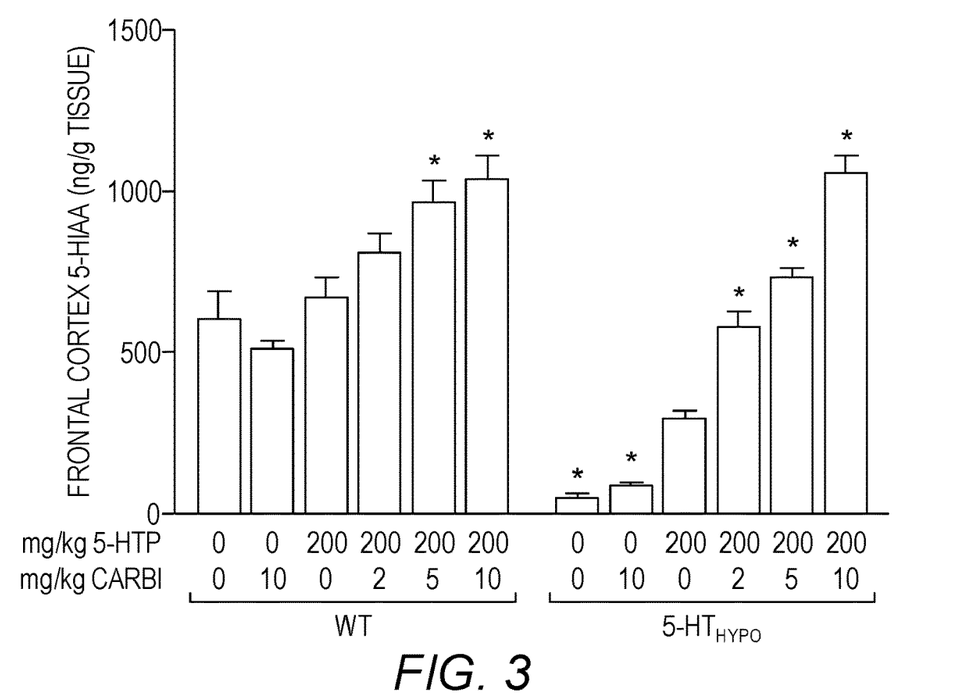
FIG. 3. Effects of low-dose carbidopa on the brain 5-HIAA tissue elevation induced by 5-HTP administration. Carbidopa dose-dependently augmented the 5-HIAA tissue elevation induced by 5-HTP. The effect was proportionally more pronounced in 5-$HT_{Hypo}$ mice, which due do their lower endogenous brain 5-HT synthesis had lower brain 5-HIAA levels at baseline. * denotes a statistically significant difference from the group only treated with 5-HTP 200 mg/kg/day. One-way ANOVA, Dunnett's post-hoc test.

5-HTP treatment elevated levels of plasma 5-HTP (FIG. 1), brain 5-HT (FIG. 2), and brain 5-HIAA (FIG. 3). Carbidopa alone, without concomitant 5-HTP treatment, had no effects. When administered in addition to 5-HTP, carbidopa manifold and dose-dependently augmented the effect of 5-HTP treatment on all outcome measures. The treatment effects on plasma 5-HTP did not differ between WT and 5-$HT_{Hypo}$ mice. This was expected, as the mutation carried by the 5 $HT_{Hypo}$ mice will not affect 5-HTP absorption and metabolism (Beaulieu et al, 2008). In contrast, the 5 HTP+/− carbidopa treatment effects on brain 5-HT and 5-HIAA were relatively more pronounced in the 5-$HT_{Hypo}$ mice. This might partly reflect that the WT mice at baseline already had high tissue levels of 5-HT. Note, previous data demonstrate that even minor elevations in tissue levels of 5-HT and 5-HIAA in WT mice translates into substantial elevations in the levels of the functionally active pool of 5 HT in the extracellular space (5-$HT_{Ext}$) (Jacobsen et al, 2016b).

Overall, these findings suggest that this 5-HTP/low-dose carbidopa treatment regimen may be particularly relevant in diseases associated with brain 5-HT dysfunction, e.g. psychiatric disorders, but also in patients and in disorders where 5-HT levels are normal and where general elevation of 5-HT and enhancement might be therapeutic. Plasma carbidopa levels were below the limit of detection, i.e. <2 ng/ml, even at 10 mg/kg/day, the highest dose.

This demonstrates that carbidopa even at doses only producing plasma exposure levels at least 12 times lower than usual systemically active levels (i.e. 25 ng/ml, Verhagen et al, 2015; Yeh et al, 1989) still markedly enhances 5-HTP bioavailability. The underlying mechanism is thought to be that the carbidopa acts only locally in the upper intestine to protect 5-HTP against first-pass metabolism during transport over the intestinal wall. First-pass metabolism of exogenously administered 5-HTP is known to be pronounced under normal circumstances (Shindo et al, 1977). Further, as it is well-established that 5-HTP's adverse effects predominantly is caused by 5-HTP conversion to 5-HT in the intestine, these data predict that this 5-HTP/low-dose carbidopa regimen will improve the safety and tolerability of 5-HTP therapy in humans.

Thus, carbidopa doses lower than previously reported can enhance 5-HTP bioavailability and pharmacodynamic (brain 5-HT) effects. Furthermore, carbidopa doses essentially only being effective in inhibiting PDI activity locally in the intestine can markedly enhance 5-HTP bioavailability and pharmacodynamic (brain 5-HT) effects. 5-HTP:carbidopa ratios of 20:1 to 100:1, far higher than in prior reports, were effective in enhancing 5-HTP bioavailability and pharmacodynamic (brain 5-HT) effects.

These data demonstrate the feasibility of a human therapeutic method of co-treatment to 5-HTP with a low-dose carbidopa (e.g. a dose of about 0.17 to 0.83 mg/kg/day to enhance 5-HTP bioavailability). Note, because of higher metabolism in mice ~12× the human daily doses are needed to produce same exposure in mice. The mouse to human 'inter-species scaling factor' is thus 1/12 (Sharma and McNeill, 2009).

These data also demonstrate the feasibility of a method of co-treatment in 5-HTTP:carbidopa ratios of 20:1 to 100:1 to enhance 5-HTP bioavailability and reduce 5-HTP GI adverse events.

REFERENCES

Agren H, Reibring L, Hartvig P, Tedroff J, Bjurling P, Hornfeldt K, et al (1991). Low brain uptake of L-[11C] 5-hydroxytryptophan in major depression: a positron emission tomography study on patients and healthy volunteers. Acta Psychiatr Scand 83(6): 449-455.

Alino J J, Gutierrez J L, Iglesias M L (1976). 5-Hydroxytryptophan (5-HTP) and a MAOI (nialamide) in the treatment of depressions. A double-blind controlled study. Int Pharmacopsychiatry 11(1): 8-15.

Appleby L, Warner R, Whitton A, Faragher B (1997). A controlled study of fluoxetine and cognitive-behavioural counselling in the treatment of postnatal depression. Bmj 314(7085): 932-936.

Asberg M (1997). Neurotransmitters and suicidal behavior. The evidence from cerebrospinal fluid studies. Ann N Y Acad Sci 836: 158-181.

Badawy A A, Bano S (2016). Tryptophan Metabolism in Rat Liver After Administration of Tryptophan, Kynurenine Metabolites, and Kynureninase Inhibitors. Int J Tryptophan Res 9: 51-65.

Bartels C, Wagner M, Wolfsgruber S, Ehrenreich H, Schneider A, Alzheimer's Disease Neuroimaging I (2018). Impact of SSRI Therapy on Risk of Conversion From Mild Cognitive Impairment to Alzheimer's Dementia in Individuals With Previous Depression. Am J Psychiatry 175(3): 232-241

Beaulieu J M, Zhang X, Rodriguiz R M, Sotnikova T D, Cools M J, Wetsel W C, et al (2008). Role of GSK3 beta in behavioral abnormalities induced by serotonin deficiency. Proceedings of the National Academy of Sciences of the United States of America 105(4): 1333-1338.

Blier P, Bergeron R (1996). Sequential administration of augmentation strategies in treatment-resistant obsessive-compulsive disorder: preliminary findings. Int Clin Psychopharmacol 11(1): 37-44.

Bowsher R.R. HDP (1986). Aromatic L-Amino Acid Decarboxylase. In: Boulton A. A. B G B, Yu P. H. (ed). Neurotransmitter Enzymes. Neuromethods (Series 1: Neurochemistry), Humana Press. Vol 5.

Brown G L, Ebert M H, Goyer P F, Jimerson D C, Klein W J, Bunney W E, et al (1982). Aggression, suicide, and serotonin: relationships to CSF amine metabolites. Am J Psychiatry 139(6): 741-746.

Bruni O, Ferri R, Miano S, Verrillo E (2004). L-5-Hydroxytryptophan treatment of sleep terrors in children. Eur J Pediatr 163(7): 402-407.

Byerley W F, Judd L L, Reimherr F W, Grosser B I (1987). 5-Hydroxytryptophan: a review of its antidepressant efficacy and adverse effects. J Clin Psychopharmacol 7(3): 127-137.

Cangiano C, Ceci F, Cascino A, Del Ben M, Laviano A, Muscaritoli M, et al (1992). Eating behavior and adherence to dietary prescriptions in obese adult subjects treated with 5-hydroxytryptophan. Am J Clin Nutr 56(5): 863-867.

Caruso I, Sarzi Puttini P, Cazzola M, Azzolini V (1990). Double-blind study of 5-hydroxytryptophan versus placebo in the treatment of primary fibromyalgia syndrome. The Journal of international medical research 18(3): 201-209.

Carver C S, Johnson S L, Joormann J (2008). Serotonergic function, two-mode models of self-regulation, and vulnerability to depression: what depression has in common with impulsive aggression. Psychol Bull 134(6): 912-943.

Claxton A J, Cramer J, Pierce C (2001). A systematic review of the associations between dose regimens and medication compliance. Clinical therapeutics 23(8): 1296-1310.

Connor K M, Sutherland S M, Tupler L A, Malik M L, Davidson J R (1999). Fluoxetine in post-traumatic stress disorder. Randomised, double-blind study. Br J Psychiatry 175: 17-22.

Coric V, Feldman H H, Oren D A, Shekhar A, Pultz J, Dockens R C, et al (2010). Multicenter, randomized, double-blind, active comparator and placebo-controlled trial of a corticotropin-releasing factor receptor-1 antagonist in generalized anxiety disorder. Depress Anxiety 27(5): 417-425.

Da Prada M, Kettler R, Zurcher G, Schaffner R, Haefely W E (1987). Inhibition of Decarboxylase and Levels of Dopa and 3-O-Methyldopa: A Comparative Study of Benserazide versus Carbidopa in Rodents and of Madopar Standard versus Madopar HBS in Volunteers. Eur Neurol 27(suppl 1): 9-20.

Freitas M E, Ruiz-Lopez M, Fox S H (2016). Novel Levodopa Formulations for Parkinson's Disease. CNS drugs 30(11): 1079-1095.

Fuller R W, Snoddy H D (1980). Effect of serotonin-releasing drugs on serum corticosterone concentration in rats. Neuroendocrinology 31(2): 96-100.

Gasser U E, Fischer A, Timmermans J P, Arnet I (2013). Pharmaceutical quality of seven generic Levodopa/Benserazide products compared with original Madopar (R)/Prolopa(R). BMC Pharmacol Toxicol 14: 24.

Gershon M D (2013). 5-Hydroxytryptamine (serotonin) in the gastrointestinal tract. Curr Opin Endocrinol Diabetes Obes 20(1): 14-21.

Gijsman H J, van Gerven J M, de Kam M L, Schoemaker R C, Pieters M S, Weemaes M, et al (2002). Placebo-controlled comparison of three dose-regimens of 5-hydroxytryptophan challenge test in healthy volunteers. J Clin Psychopharmacol 22(2): 183-189.

Guerdjikova A I, McElroy S L, Kotwal R, Welge J A, Nelson E, Lake K, et al (2008). High-dose escitalopram in the treatment of binge-eating disorder with obesity: a placebo-controlled monotherapy trial. Hum Psychopharmacol 23(1): 1-11.

Hsu A, Yao H M, Gupta S, Modi N B (2015). Comparison of the pharmacokinetics of an oral extended-release capsule formulation of carbidopa-levodopa (IPX066) with immediate-release carbidopa-levodopa (Sinemet), sustained-release carbidopa-levodopa (Sinemet CR), and carbidopa-levodopa-entacapone (Stalevo). Journal of clinical pharmacology.

Jackson C W, Cates M, Lorenz R (2010). Pharmacotherapy of eating disorders. Nutr Clin Pract 25(2): 143-159.

Jacobsen J P, Krystal A D, Krishnan K R, Caron M G (2016a). Adjunctive 5-Hydroxytryptophan Slow-Release for Treatment-Resistant Depression: Clinical and Preclinical Rationale. Trends Pharmacol Sci.

Jacobsen J P, Medvedev I O, Caron M G (2012a). The 5-HT deficiency theory of depression: perspectives from a naturalistic 5-HT deficiency model, the tryptophan hydroxylase 2Arg439His knockin mouse. Philos Trans R Soc Lond B Biol Sci 367(1601): 2444-2459.

Jacobsen J P, Rudder M L, Roberts W, Royer E L, Robinson T J, Oh A, et al (2016b). SSRI Augmentation by 5-Hydroxytryptophan Slow Release: Mouse Pharmacodynamic Proof of Concept. Neuropsychopharmacology 41(9): 2324-2334.

Jacobsen J P, Siesser W B, Sachs B D, Peterson S, Cools M J, Setola V, et al (2012b). Deficient serotonin neurotransmission and depression-like serotonin biomarker alterations in tryptophan hydroxylase 2 (Tph2) loss-of-function mice. Molecular psychiatry 17(7): 694-704.

Jacobsen JPRD, NC, US), Caron, Marc G. (Hillsborough, N.C., US) (2016). Slow-release formulations of 5-hydroxytryptophan as an adjunct to pro-serotonergic therapies. Duke University (Durham, N.C., US): United States.

Kahn R S, Westenberg H G, Verhoeven W M, Gispen-de Wied C C, Kamerbeek W D (1987). Effect of a serotonin precursor and uptake inhibitor in anxiety disorders; a double-blind comparison of 5-hydroxytryptophan, clomipramine and placebo. Int Clin Psychopharmacol 2(1): 33-45.

Lader M, Stender K, Burger V, Nil R (2004). Efficacy and tolerability of escitalopram in 12- and 24-week treatment of social anxiety disorder: randomised, double-blind, placebo-controlled, fixed-dose study. Depress Anxiety 19(4): 241-248.

Lopes C M, Bettencourt C, Rossi A, Buttini F, Barata P (2016). Overview on gastroretentive drug delivery systems for improving drug bioavailability. Int J Pharm 510(1): 144-158.

Lowe S L, Yeo K P, Teng L, Soon D K, Pan A, Wise S D, et al (2006). L-5-Hydroxytryptophanaugments the neuroendocrine response to a SSRI. Psychoneuroendocrinology 31(4): 473-484.

Manegold C, Hoffmann G F, Degen I, Ikonomidou H, Knust A, Laass M W, et al (2009). Aromatic L-amino acid decarboxylase deficiency: clinical features, drug therapy and follow-up. J Inherit Metab Dis 32(3): 371-380.

Mead G E, Hsieh C F, Lee R, Kutlubaev M, Claxton A, Hankey G J, et al (2013). Selective serotonin reuptake inhibitors for stroke recovery: a systematic review and meta-analysis. Stroke; a journal of cerebral circulation 44(3): 844-850.

Merck (2018). SINEMET® CR. Vol 2018.

Mitra B, Chang J, Wu S J, Wolfe C N, Ternik R L, Gunter T Z, et al (2017). Feasibility of mini-tablets as a flexible drug delivery tool. Int J Pharm 525(1): 149-159.

Nicolodi M, Sicuteri F (1999). L-5-hydroxytryptophan can prevent nociceptive disorders in man. Adv Exp Med Biol 467: 177-182.

Nokhodchi A, Raja S, Patel P, Asare-Addo K (2012). The role of oral controlled release matrix tablets in drug delivery systems. Bioimpacts 2(4): 175-187.

Pahwa R, Lyons K E, Hauser R A, Fahn S, Jankovic J, Pourcher E, et al (2014). Randomized trial of IPX066, carbidopa/levodopa extended release, in early Parkinson's disease. Parkinsonism Relat Disord 20(2): 142-148.

Perry K W, Fuller R W (1993). Extracellular 5-hydroxytryptamine concentration in rat hypothalamus after administration of fluoxetine plus L-5-hydroxytryptophan. J Pharm Pharmacol 45(8): 759-761.

Rauws A G, Vos J G, Garbis-Berkvens J M, Peters P W, de Vries T, van Logten M J (1982). Comparative 90-day toxicity of two decarboxylase inhibitors, benserazide and carbidopa, in the rat. Toxicol Appl Pharmacol 66(2): 201-220.

Rose S, Jenner P, Marsden C D (1988). The effect of carbidopa on plasma and muscle levels of L-dopa, dopamine, and their metabolites following L-dopa administration to rats. Mov Disord 3(2): 117-125.

Sargent P A, Williamson D J, Cowen P J (1998). Brain 5-HT neurotransmission during paroxetine treatment. The British journal of psychiatry: the journal of mental science 172: 49-52.

Sharma V, McNeill J H (2009). To scale or not to scale: the principles of dose extrapolation. Br J Pharmacol 157(6): 907-921.

Shindo H, Komai T, Kawai K (1977). Mechanism of intestinal absorption and brain uptake of L-5-hydroxytryptophan in rats, as compared to those of L-3,4-dihydroxyphenylalanine. Chem Pharm Bull (Tokyo) 25(6): 1417-1425.

Sloan R L, Brown K W, Pentland B (1992). Fluoxetine as a treatment for emotional lability after brain injury. Brain Inj 6(4): 315-319.

Soulairac A, Lambinet H (1977). [Effect of 5-hydroxytryptophan, a serotonin precursor, on sleep disorders]. Ann Med Psychol (Paris) 1(5): 792-798.

Steiner M, Steinberg S, Stewart D, Carter D, Berger C, Reid R, et al (1995). Fluoxetine in the treatment of premenstrual dysphoria. Canadian Fluoxetine/Premenstrual Dysphoria Collaborative Study Group. N Engl J Med 332 (23): 1529-1534.

Takahashi S, Takahashi R, Masumura I, Miike A (1976). Measurement of 5-hydroxyindole compounds during L-5-HTP treatment in depressed patients. Folia Psychiatr Neurol Jpn 30(4): 463-473.

Thombre A G, Appel L E, Chidlaw M B, Daugherity P D, Dumont F, Evans L A, et al (2004). Osmotic drug delivery using swellable-core technology. J Control Release 94(1): 75-89.

Trouillas P, Brudon F, Adeleine P (1988). Improvement of cerebellar ataxia with levorotatory form of 5-hydroxytryptophan. A double-blind study with quantified data processing. Arch Neurol 45(11): 1217-1222.

Turner E H, Loftis J M, Blackwell A D (2006a). Serotonin a la carte: supplementation with the serotonin precursor 5-hydroxytryptophan. Pharmacol Ther 109(3): 325-338.

Turner E H, Loftis J M, Blackwell A D (2006b). Serotonin a la carte: supplementation with the serotonin precursor 5-hydroxytryptophan. Pharmacol Ther 109(3): 325-338.

van Hiele L J (1980). 1-5-Hydroxytryptophan in depression: the first substitution therapy in psychiatry? The treatment of 99 out-patients with 'therapy-resistant' depressions. Neuropsychobiology 6(4): 230-240.

van Praag H M (1982). Serotonin precursors in the treatment of depression. Advances in biochemical psychopharmacology 34: 259-286.

Van Woert M H, Rosenbaum D, Howieson J, Bowers M B, Jr. (1977). Long-term therapy of myoclonus and other neurologic disorders with L-5-hydroxytryptophan and carbidopa. The New England journal of medicine 296(2): 70-75.

Veenstra-VanderWeele J, Muller C L, Iwamoto H, Sauer J E, Owens W A, Shah C R, et al (2012). Autism gene variant causes hyperserotonemia, serotonin receptor hypersensitivity, social impairment and repetitive behavior. Proceedings of the National Academy of Sciences of the United States of America 109(14): 5469-5474.

Verhagen Metman L, Stover N, Chen C, Cowles V E, Sweeney M (2015). Gastroretentive carbidopa/levodopa, DM-1992, for the treatment of advanced Parkinson's disease. Mov Disord 30(9): 1222-1228.

Viscogliosi G, Chiriac I M, Ettorre E (2017). Efficacy and Safety of Citalopram Compared to Atypical Antipsychotics on Agitation in Nursing Home Residents With Alzheimer Dementia. J Am Med Dir Assoc 18(9): 799-802.

Westenberg H G, Gerritsen T W, Meijer B A, van Praag H M (1982). Kinetics of 1-5-hydroxytryptophan in healthy subjects. Psychiatry Res 7(3): 373-385.

Yeh K C, August T F, Bush D F, Lasseter K C, Musson D G, Schwartz S, et al (1989). Pharmacokinetics and bioavailability of Sinemet C R: a summary of human studies. Neurology 39(11 Suppl 2): 25-38.

Yoshimura M, Kambara S, Takahashi H, Okabayashi H, Ijichi H (1987). Involvement of dopamine in development of hypertension in spontaneously hypertensive rat: effect of carbidopa, inhibitor of peripheral dopa decarboxylase. Clin Exp Hypertens A 9(10): 1585-1599.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of enhancing bioavailability of enterally administered 5-HTP in a human subject in need thereof, said method comprising:
   enterally co-administering low-dose carbidopa with said 5-HTP, said low-dose carbidopa provided in a daily dosage of from about 0.1 to about 0.8 mg/kg/day or about 5 mg to about 60 mg per day to thereby enhance the bioavailability of the enterally administered 5-HTP,
   wherein the 5-HTP and low-dose carbidopa are administered in a daily dosage ratio of from 100:1 to 20:1 of 5-HTP:carbidopa,
   wherein the 5-HTP and low-dose carbidopa are provided in a slow-release (SR) formulation of the 5-HTP and a SR formulation of the low-dose carbidopa, and
   wherein the 5-HTP and low-dose carbidopa are administered orally, in the same or separate dosage forms.

2. The method of claim 1, wherein upon enterally co-administering the low-dose carbidopa, the subject has blood plasma levels of carbidopa of less than 25 ng/ml.

3. The method of claim 1, wherein the 5-HTP and low-dose carbidopa are administered once, twice, or three times per day.

4. The method of claim 1, wherein the SR formulation is a gastroretentive formulation.

5. The method of claim 4, wherein the 5-HTP and low-dose carbidopa are co-administered with a meal.

6. The method of claim 1, wherein said subject is in need of treatment for depression, social anxiety, panic disorder, generalized anxiety disorder, OCD, impulse control disorders, suicidality, borderline personality disorder, fibromyalgia, ataxia, mood, cognitive, or behavioral symptoms and agitation related to neurological disorders, stroke recovery, autism, migraine, sleep disorders, premenstrual dysphoria, post-traumatic stress disorder, post-partum depression, or depression after interferon treatment.

7. The method of claim 1, wherein said subject is in need of treatment for a psychiatric disorder and/or neurologic disorder, such as a mood anomaly or anomaly in impulse or aggression control.

8. The method of claim 1, wherein said subject is in need of treatment for depression, anxiety, obesity, suicidality, obsessive compulsive disorder, or ADHD.

9. The method of claim 1, wherein said subject is in need of treatment for depression, major depressive disorder or treatment-resistant depression.

10. The method of claim 1, wherein the method comprises monotherapy with the 5-HTP and carbidopa.

11. The method of claim 1, wherein the method comprises adjunctive therapy with the 5-HTP and carbidopa along with a serotonin enhancer.

12. The method of claim 11, wherein said serotonin enhancer is selected from the group consisting of serotonin reuptake inhibitors, serotonin norepinephrine reuptake inhibitors, triple-reuptake inhibitors, monoamine oxidase inhibitors, tricyclic antidepressants, serotonin agonists, amphetamines, serotonin precursors, serotonin prodrugs, intermediates in the biosynthesis of serotonin, and pharmaceutically acceptable salts thereof.

13. The method of claim 11, wherein said serotonin enhancer is a selective serotonin reuptake inhibitor (SSRI).

14. The method of claim 11, wherein said serotonin enhancer is selected from the group consisting of: citalopram, dapoxetine, escitalopram, fluoxetine, fluvoxamine, indalpine, paroxetine, sertraline, vilazodone, vortioxetine, zimelidine and combinations thereof.

15. The method of claim 1, wherein said low-dose carbidopa is provided in a daily dosage of from about 0.1 to about 0.5 mg/kg/day.

16. The method of claim 1, wherein said 5-HTP is provided in a daily dosage of from about 0.1 gram per day, to about 6 grams per day.

17. The method of claim 1, wherein said low-dose carbidopa provided in a daily dosage of from about 5 mg to about 35 mg per day.

18. The method of claim 1, wherein upon enterally co-administering the low-dose carbidopa, the subject has blood plasma levels of carbidopa of less than 10 ng/ml.

19. The method of claim 1, wherein upon enterally co-administering the low-dose carbidopa, the subject has blood plasma levels of carbidopa of less than 5 ng/ml.

20. The method of claim 1, wherein upon enterally co-administering the low-dose carbidopa, the subject has blood plasma levels of carbidopa of less than 2 ng/ml.

21. The method of claim 1, wherein said 5-HTP is provided in a daily dosage of from about 0.2 gram per day, to about 1 gram per day.

22. The method of claim 1, wherein said 5-HTP is provided in a daily dosage of about 0.5 gram per day.

* * * * *

UNITED STATES PATENT AND TRADEMARK OFFICE
CERTIFICATE OF CORRECTION

PATENT NO. : 11,337,963 B2
APPLICATION NO. : 15/733423
DATED : May 24, 2022
INVENTOR(S) : Jacobsen et al.

It is certified that error appears in the above-identified patent and that said Letters Patent is hereby corrected as shown below:

In the Specification

Column 8, Line 41: delete "$T_m$" and insert --$T_{max}$--

Signed and Sealed this
Twenty-seventh Day of December, 2022

Katherine Kelly Vidal
*Director of the United States Patent and Trademark Office*